United States Patent [19]

Kay et al.

[11] Patent Number: 4,782,075
[45] Date of Patent: Nov. 1, 1988

[54] HEXAHYDROCARBAZOLE CONTAINING ALKYLAMINOAMIDE COMPOUNDS, PHARMACEUTICAL COMPOSITIONS AND USE

[75] Inventors: David P. Kay, Purton Swindon; Peter D. Kennewell, Okus Swindon, both of Great Britain

[73] Assignee: Roussel Uclaf, Paris, France

[21] Appl. No.: 883,914

[22] Filed: Jul. 10, 1986

[30] Foreign Application Priority Data

Jul. 15, 1985 [GB] United Kingdom ............... 8517854

[51] Int. Cl.$^4$ .................... A61K 31/40; C07D 209/88
[52] U.S. Cl. ..................................... 514/411; 548/439
[58] Field of Search ........................ 548/439; 514/411

[56] References Cited
U.S. PATENT DOCUMENTS 4,254,134 3/1981 Fliedner, Jr. ..................... 548/439

Primary Examiner—Robert W. Ramsuer
Attorney, Agent, or Firm—Bierman and Muserlian

[57] ABSTRACT

Novel alkylaminoamides of the formula

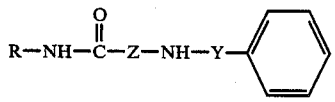

I wherein R is selected from the group consisting of (a) alkyl of 1 to 8 carbon atoms, (b) cycloalkyl of 3 to 7 carbon atoms optionally substituted with phenyl, (c) aryl of 6 to 14 carbon atoms optionally substituted with at least one member of the group consisting of halogen, —CF$_3$, alkyl of 1 to 6 carbon atoms, —NO$_2$ and cycloalkyl of 3 to 7 carbon atoms, (d) aralkyl of 7 to 14 carbon atoms and (e)

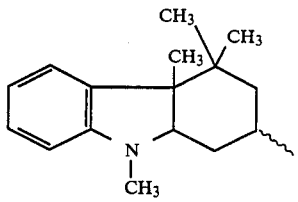

Z is —(CH$_2$)$_n$— optionally substituted by an alkyl of 1 to 6 carbon atoms, n is an integer from 1 to 6, Y is —(CH$_2$)$_n$— or

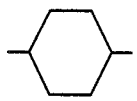

and their non-toxic, pharmaceutically acceptable acid addition salts having remarkable anti-oedematous and anti-inflammatory activity.

12 Claims, No Drawings

HEXAHYDROCARBAZOLE CONTAINING ALKYLAMINOAMIDE COMPOUNDS, PHARMACEUTICAL COMPOSITIONS AND USE

OBJECTS OF THE INVENTION

It is an object of the invention to provide the novel compounds of formula I and their non-toxic, pharmaceutically acceptable addition salts and a process and intermediates for their preparations.

It is another object of the invention to provide novel anti-edematous and anti-inflammatory compositions and a method of relieving edemas and inflammation in warm-blooded animals.

These and other objects and advantages of the invention will become obvious from the following detailed description.

THE INVENTION

The novel compounds of the invention are selected from the group consisting of alkylaminoamides of the formula

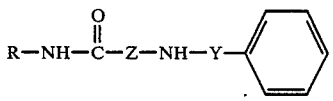

wherein R is selected from the group consisting of (a) alkyl of 1 to 8 carbon atoms, (b) cycloalkyl of 3 to 7 carbon atoms optionally substituted with phenyl, (c) aryl of 6 to 14 carbon atoms optionally substituted with at least one member of the group consisting of halogen, —CF$_3$, alkyl of 1 to 6 carbon atoms, —NO$_2$ and cycloalkyl of 3 to 7 carbon atoms, (d) aralkyl of 7 to 14 carbon atoms and (e)

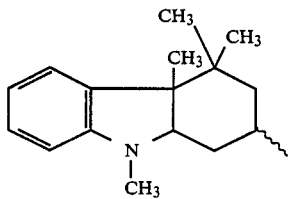

Z is —(CH$_2$)$_n$— optionally substituted by an alkyl of 1 to 6 carbon atoms, n is an integer from 1 to 6, Y is —(CH$_2$)$_n$— or

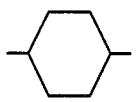

and their non-toxic, pharmaceutically acceptable acid addition salts.

Examples of alkyls of 1 to 8 carbon atoms are methyl, ethyl, n-propyl, isopropyl and linear and branched butyl, hexyl, pentyl, heptyl and octyl and examples of cycloalkyls of 3 to 7 carbon atoms are cyclopropyl, cyclobutyl, cyclopentyl, cyclohexyl and cycloheptyl.

Examples of aryl of 6 to 14 carbon atoms are phenyl and naphthyl, both optionally substituted with at least one member of the group consisting of fluorine, chlorine, bromine, —CF$_3$, —NO$_2$, alkyl of 1 to 6 carbon atoms and cycloalkyl of 3 to 7 carbon atoms. Examples of aralkyl of 7 to 14 carbon atoms are benzyl, phenethyl, phenylpropyl, phenylbutyl, phenylpentyl and phenylhexyl.

Examples of suitable acids for the formation of non-toxic, pharmaceutically acceptable acid addition salts are inorganic acids such as hydrochloric acid, hydrobromic acid, sulfuric acid, nitric acid and phosphoric acid and organic acids such as fumaric acid, acetic acid, propionic acid, glyoxylic acid, fumaric acid, oxalic acid, aspartic acid, alkylsulfonic acids such as methane sulfonic acid and ethane sulfonic acid, aryl sulfonic acids such as benzene sulfonic acid and p-toluene sulfonic acid and aryl carboxylic acids such as benzoic acid.

Among the preferred compounds of formula I are those wherein R is (1,2,3,4,4a,9a-hexahydro-4,4,4a,9-tetramethylcarbazol-2α-yl), (1,2,3,4,4a,9a-hexahydro-4,4,4a,9-tetramethylcarbazol-2β-yl), n-hexyl, cyclohexyl, phenylcyclohexyl or phenyl, or a phenyl substituted by one or two substituents selected from chlorine, cyclohexyl, trifluoromethyl and nitro groups; those wherein Z is —CH$_2$—, —(CH$_2$)$_2$— or —(CH$_2$)$_3$— and those wherein Y is

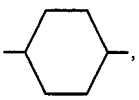

—(CH$_2$)$_3$— or —(CH$_2$)$_4$— and their non-toxic, pharmaceutically acceptable acid addition salts.

Particularly preferred are compounds of formula I wherein R is (1,2,3,4,4a,9a-hexahydro-4,4,4a,9-tetramethylcarbazol-2α-yl), (1,2,3,4,4a,9a-hexahydro-4,4,4a,9-tetramethylcarbazol-2β-yl) or a substituted phenyl; Z is —(CH$_2$)$_2$— and Y is

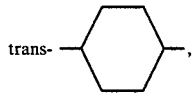

or —(CH$_2$)$_4$— and their acid addition salts thereof.

Among specific preferred compounds of the invention are

N-(1,2,3,4,4a,9a-hexahydro-4,4,4a,9-tetramethylcarbazol-2β-yl)-3-(trans-4-phenylcyclohexylamino)-propionamide;

N-(1,2,3,4,4a,9a-hexahydro-4,4,4a,9-tetramethylcarbazol-2β-yl)-2-(trans-4-phenylcyclohexylamino)-acetamide;

N-(1,2,3,4,4a,9a-hexahydro-4,4,4a,9-tetramethylcarbazol-2α-yl)-3-(4-phenylbutylamino)-propionamide;

N-(1,2,3,4,4a,9a-hexahydro-4,4,4a,9-tetramethyl-carbazol-2β-yl)-3-(3-phenylpropylamino)-propionamide;

N-(1,2,3,4,4a,9a-hexahydro-4,4,4a,9-tetramethylcarbazol-2α-yl)-2-(4-phenylbutylamino)-acetamide;

N-cyclohexyl-3-(trans-4-phenylcycyohexylamino)-propionamide;

N-phenyl-3-(trans-4-phenylcyclohexylamino)-propionamide;

N-n-hexyl-3-(trans-4-phenylcyclohexylamino)-propionamide; and

N-(4-chlorophenyl)-3-(trans-4-phenylcyclohexylamino)-propionamide, and their non-toxic, pharmaceutically acceptable acid addition salts.

The novel process of the invention for the preparation of the compounds of formula I comprises reacting a compound of the formula R—NH—CO—Z—Hal  IV wherein R and Z have the above definitions and Hal is chlorine or bromine with a compound of the formula

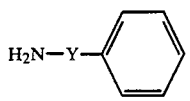  V wherein Y has the above definitions. The reaction is conveniently carried out in the presence of an organic solvent such as for example, an aromatic solvent like benzene or toluene.

The starting compounds of formula IV may be prepared by reacting an amine of the formula

R—NH$_2$  II wherein R has the above definition with a compound of the formula

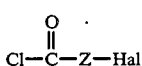  III wherein Z and Hal have the above definitions in the presence of an acid binding agent such as potassium carbonate. The reaction may be effected in an organic solvent such as dichloromethane.

The compounds of formula I are basic in character and may subsequently, if desired, be converted into the acid addition salts thereof, particularly the physiologically acceptable acid addition salts thereof with inorganic or organic acids by conventional methods such as by reacting the compounds as bases with a solution of a stoichiometric amount of the corresponding acid in a suitable solvent. Such salts may be prepared in situ in the reaction mixture without the necessity for intermediate isolation of the free bases themselves. Conversely the acid addition salts of the compounds of formula I obtained may, if desired, subsequently be converted into compounds of formula I or into further acid addition salts thereof.

Of the compounds of formula II, 2-amino-1,2,3,4,4a,-9a-hexahydro-4,4,4a,9-tetramethylcarbazole is new and constitutes a further object of the present invention. It may be prepared by the action of sodium cyanoborohydride on 3,4,4a,9a-tetrahydro-4,4,4a,9-tetramethylcarbazol-2-(1H)-one in the presence of a source of ammonia such as ammonium acetate.

The novel anti-edematous and anti-inflammatory compositions of the invention are comprised of an antiedematously and anti-inflammatorily effective amount of at least one compound of formula I and their non-toxic, pharmaceutically acceptable acid addition salts and an inert pharmaceutical carrier or excipient. The compositions may be in the form of tablets, dragees, capsules, granules, ampoules, suppositories and injectable solutions or suspensions.

Examples of suitable excipients are talc, gum arabic, lactose, starch, magnesium stearate, cocoa butter, aqueous or non-aqueous vehicles, animal or vegetable fats, paraffin derivatives, glycols, various wetting, dispersing or emulsifying agents and/or preservatives.

The compositions possess remarkable antiedematous and anti-inflammatory activity and are therefore useful for the treatment of inflammatory diseases.

The novel method of the invention for treating edema and inflammation in warm-blooded animals, including humans, comprises administering to warm-blooded animals an antiedematously and anti-inflammatorily effective amount of at least one compound of formula I and their non-toxic, pharmaceutically acceptable acid addition salts. The active compounds may be administered orally, rectally, or parenterally. The usual daily dose is 0.001 to 1.4 mg/kg depending on the specific compound, the method of administration and the condition treated.

In the following examples there are described several preferred embodiments to illustrate the invention. However, it is to be understood that the invention is not intended to be limited to the specific embodiments.

EXAMPLE 1

N-(1,2,3,4,4a,9a-hexahydro-4,4,4a,9-tetramethylcarbazol-2β-yl)-3-(trans-4-phenylcyclohexylamino)-propionamide and its hydrochloride

STEP A:
2-amino-1,2,3,4,4a,9a-hexahydro-4,4,4a,9-tetramethyl carbazole

A mixture of 22 g of 3,4,4a,9a-tetrahydro-4,4,4a,9-tetramethylcarbazol-2-(1H)-one prepared as in J. Chem. Soc., 1955, 4369, 37 g of ammonium acetate and 4 g of sodium cyanoborohydride in 300 ml of methanol was stirred overnight at room temperature under nitrogen. The mixture was concentrated to 70 ml, diluted with 600 ml of water, acidified to pH of 1 with concentrated HCl and stirred at room temperature for 1 hour. The mixture was extracted with ether, adjusted to a pH of 5 with concentrated ammonia, further extracted with ether and then adjusted to a pH of 10 with concentrated ammonia. Extraction with ether then gave 11 g of a 50% mixture of α- and β-2-amino-1,2,3,4,4a,9a-hexahydro-4,4,4a,9-tetramethylcarbazole as a pale yellow oil.

STEP B:
N-(1,2,3,4,4a,9a-hexahydro-4,4,4a,9-tetramethylcarbazol-2β-yl)-3-chloropropionamide A mixture of 24.4 g of 2-amino-1,2,3,4,4a,9a-hexahydro-4,4,4a,9-tetramethylcarbazole and 25 g of potassium carbonate was stirred in 300 ml of dichloromethane while 14 g of 3-chloropropionyl chloride were added dropwise. The mixture was stirred overnight at room temperature and poured into water. The organic layer was washed with 2N hydrochloric acid and aqueous sodium bicarbonate, dried over MgSO$_4$ and evaporated to dryness to give a colorless solid. The solid was subjected to HPLC on "Lichoprep" in dichloromethane to yield first 6 g (18%) of N-(1,2,3,4,4a,9a-hexahydro-4,4,4a,9-tetramethylcarbazol-2β-yl)-3-chloropropionamide melting at 168°–70° C., $\nu_{max}$ 3260 and 1630 cm$^{-1}$, and then 12 g (36%) of N-(1,2,3,4,4a,9a-hexahydro-4,4,4a,9-tetramethylcarbazol-2α-yl)-3-chloropropionamide melting at 166°–8° C., $\nu_{max}$ 3215 and 1630 cm$^{-1}$.

STEP C:

N-(1,2,3,4,4a,9a-hexahydro-4,4,4a,9-tetramethylcarbazol-2β-yl)-3-(trans-4-phenylcyclohexylamino)-propionamide 1.5 g of N-(1,2,3,4,4a,9a-hexahydro-4,4,4a,9-tetramethylcarbazol-2β-yl)-3-chloropropionamide and 3 g of trans-4-phenylcyclohexylamine prepared as in J. Org. Chem. (1952) 17, 1017 were stirred under reflux in dry toluene for 3 days. The cooled reaction mixture was filtered and evaporated to dryness under reduced pressure. The residue was chromatographed on silica and elution with dichloromethane-methanol (95:5) gave 1.36 g (66%) of N-(1,2,3,4,4a,9a-hexahydro-4,4,4a,9-tetramethylcarbazol-2β-yl)-3-(trans-4-phenylcyclohexylamino)-propionamide as a colorless oil. The oil was dissolved in methanol and treated with ethereal hydrogen chloride to give the colorless, hydroscopic, crystalline hydrochloride salt melting at 184°-6° C. $\nu_{max}$. 3410, 3265, 1680 cm$^{-1}$.

EXAMPLES 2 TO 20

Using the process of Example 1 but starting from the appropriate amines of formulae II and V and acid chlorides of formula III, the following compounds were prepared:

Example 2: N-(1,2,3,4,4a,9a-hexahydro-4,4,4a,9-tetramethylcarbazol-2α-yl)-3-(trans-4-phenylcyclohexylamino)-propionamide.

Example 3: N-(1,2,3,4,4a,9a-hexahydro-4,4,4a,9-tetramethylcarbazol-2β-yl)2-(trans-4-phenylcyclohexylamino)-acetamide.

Example 4: N-(1,2,3,4,4a,9a-hexahydro-4,4,4a,9-tetramethylcarbazol-2α-yl)-2-(trans-4-phenylcyclohexylamino)-acetamide.

Example 5: N-(1,2,3,4,4a,9a-hexahydro-4,4,4a,9-tetramethylcarbazol-2β-yl)-3-(4-phenylbutylamino)-propionamide.

Example 6: N-(1,2,3,4,4a,9a-hexahydro-4,4,4a,9-tetramethylcarbazol-2α-yl)-3-(4-phenylbutylamino)-propionamide.

Example 7: N-(1,2,3,4,4a,9a-hexahydro)-4,4,4a,9-tetramethylcarbazol-2β-yl)-3-(3-phenylpropylamino)-propionamide.

Example 8: N-(1,2,3,4,4a,9a-hexahydro-4,4,4a,9-tetramethylcarbazol-2α-yl)-3-(3-phenylpropylamino)-propionamide.

Example 9: N-(1,2,3,4,4a,9a-hexahydro-4,4,4a,9-tetramethylcarbazol-2β-yl)-2-(4-phenylbutylamino)-acetamide.

Example 10: N-(1,2,3,4,4a,9a-hexahydro-4,4,4a,9-tetramethylcarbazol-2α-yl)-2-(4-phenylbutylamino)-acetamide.

Example 11: N-cyclohexyl-3-(trans-4-phenylcyclohexylamino)-propionamide.

Example 12: N-phenyl-3-(trans-4-phenylcyclohexylamino)-propionamide.

Example 13: N-n-hexyl-3-(trans-4-phenylcyclohexylamino)-propionamide.

Example 14: N-(4-chlorophenyl)-3-(trans-4-phenylcyclohexylamino)-propionamide.

Example 15: N-(4-cyclohexylphenyl)-3-(trans-4-phenylcyclohexylamino)-propionamide.

Example 16: N-(3,4-dichlorophenyl)-3-(trans-4-phenylcyclohexylamino)-propionamide.

Example 17: N-(4-phenylcyclohexyl)-3-(trans-4-phenylcyclohexylamino)-propionamide.

Example 18: N-(3-trifluoromethyl-4-chlorophenyl)-3-(trans-4-phenylcyclohexylamino)-propionamide.

Example 19: N-(4-chlorophenyl)-4-(trans-4-phenylcyclohexylamino)-butyramide

Example 20: N-(3-trifluoromethyl-4-nitrophenyl)-3-(trans-4-phenylcyclohexylamino)-propionamide.

The properties of the said products are reported in the following Table.

TABLE I

RNHCO—Z—NH—Y—⟨phenyl⟩

| Ex | R | Z | Y | % | IR(KBr)cm$^{-1}$ | MP |
|---|---|---|---|---|---|---|
| 1 | β-tetramethylcarbazolyl | (CH$_2$)$_2$ | trans cyclohexyl | 66 | 3410,3265,1680,1660 | 184–6° |
| 2 | α-tetramethylcarbazolyl | " | " | 85 | 3390,1650,1600 | glass |
| 3 | β-tetramethylcarbazolyl | CH$_2$ | " | 98 | 3400,3300,1655,1600 | 155–6° |

TABLE I-continued

RNHCO—Z—NH—Y—[phenyl]

| No. | R (structure) | Z | Y | Yield % | IR | mp |
|---|---|---|---|---|---|---|
| 4 | α-1,1,9a-trimethyl-9-methyl-octahydrocarbazole | " | " | 70 | 3300,1650 | glass |
| 5 | β-1,1,9a-trimethyl-9-methyl-octahydrocarbazole-CH | (CH₂)₂ | (CH₂)₄ | 60 | 3400,3220,1650 | glass |
| 6 | α-1,1,9a-trimethyl-9-methyl-octahydrocarbazole | " | " | 75 | 3280,1640,1600 | glass |
| 7 | β-1,1,9a-trimethyl-octahydrocarbazole | " | (CH₂)₃ | 64 | 3400,3250,1650 | glass |
| 8 | α-1,1,9a-trimethyl-9-methyl-octahydrocarbazole | " | " | 46 | 3280,1640,1600 | glass |
| 9 | β-1,1,9a-trimethyl-9-methyl-octahydrocarbazole | CH₂ | (CH₂)₄ | 54 | 3300,1650,1600 | glass |
| 10 | α-1,1,9a-trimethyl-9-methyl-octahydrocarbazole | " | " | 59 | 3320,1660,1640,1600 | glass |
| 11 | cyclohexyl | (CH₂)₂ | trans-cyclohexyl | 27 | 3340,1640 | 220°(dec) |
| 12 | phenyl | " | " | 84 | 3323,3000–2300,1665 | 195°(dec) |
| 13 | CH₃(CH₂)₅ | " | " | 27 | 3300,1640 | 180°(dec) |

TABLE I-continued

RNHCO—Z—NH—Y—C₆H₄—

| Ex | R | Z | Y | Yield % | IR (cm⁻¹) | mp |
|---|---|---|---|---|---|---|
| 14 | 4-Cl-C₆H₄ | " | " | 38 | 3240,3200,3160,3100-2300,1680,1665 | 220°(dec) |
| 15 | 4-cyclohexyl-C₆H₄ | " | " | 40 | 3320,1665 | 265°(dec) |
| 16 | 3,4-diCl-C₆H₃ | " | " | 49 | 3235,3160,1680 | 211–3° |
| 17 | 4-phenylcyclohexyl | " | " | 30 | 3340,1637 | 262–4(dec) |
| 18 | 4-Cl-3-CF₃-C₆H₃ | " | " | 50 | 1686,1600 | 210–3° |
| 19 | 4-Cl-C₆H₄ | (CH₂)₃ | " | 6 | 3320,1655 | 270°(dec) |
| 20 | 4-NO₂-3-CF₃-C₆H₃ | (CH₂)₂ | " | 52 | 2920,1690 | 268–70° |

| Ex | Formula | MW | C | H | N | Cl | |
|---|---|---|---|---|---|---|---|
| 1 | | | | | | | |
| 2 | C₃₁H₄₃N₃O·½H₂O | 482.7 | 77.13 / 77.43 | 9.19 / 9.09 | 8.70 / 8.70 | | |
| 3 | C₃₀H₄₁N₃O·2HCl | 532.6 | 67.66 / 67.93 | 8.14 / 8.12 | 7.89 / 7.85 | | |
| 4 | C₃₀H₄₁N₃O | 459.7 | 78.39 / 77.91 | 8.99 / 9.00 | 9.14 / 9.06 | | |
| 5 | C₂₉H₄₁N₃O | 447.7 | 76.94 / 76.98 | 9.15 / 9.14 | 9.17 / 9.26 | | Theory + 1.3% CH₂Cl₂ |
| 6 | C₂₉H₄₁N₃O | 447.7 | 76.89 / 76.92 | 9.14 / 9.13 | 9.08 / 9.25 | | Theory + 1.4% CH₂Cl₂ |
| 7 | C₂₈H₃₉N₅O | 433.6 | | | | | |
| 8 | C₂₈H₃₉N₃O | 433.6 | | | | | |
| 9 | C₂₈H₃₉N₃O | 433.6 | 77.16 / 77.27 | 9.12 / 9.03 | 9.58 / 9.63 | | Theory + 0.6% CH₂Cl₂ |
| 10 | C₂₈H₃₉N₃O | 433.6 | 76.08 / 76.36 | 8.87 / 8.89 | 9.47 / 9.50 | | Theory + 2.0% CH₂Cl₂ |
| 11 | C₂₁H₃₂N₂O·HCl | 365.0 | 69.11 / 69.18 | 9.11 / 9.02 | 7.68 / 7.45 | 9.71 / 9.63 | |
| 12 | C₂₁H₂₆N₂O·HCl | 358.9 | 70.28 / 70.36 | 7.58 / 7.54 | 7.80 / 7.62 | 9.88 / 9.87 | |
| 13 | C₂₁H₃₄N₂O·HCl | 367.0 | 68.73 / 68.84 | 9.61 / 9.53 | 7.63 / 7.63 | 9.66 / 9.75 | |
| 14 | C₂₁H₂₅N₂OCl·HCl | 393.4 | 64.12 / 64.05 | 6.66 / 6.66 | 7.12 / 7.13 | 18.03 / 18.00 | |
| 15 | C₂₇H₃₆N₂O·HCl | 441.1 | 73.53 / 73.55 | 8.46 / 8.44 | 6.35 / 6.33 | 8.04 / 8.18 | |

TABLE I-continued

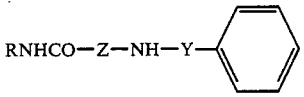

| | | | | | | | |
|---|---|---|---|---|---|---|---|
| 16 | $C_{21}H_{24}N_2OCl_2 \cdot HCl$ | 427.8 | 58.96 | 5.89 | 6.55 | 24.86 | |
| | | | 59.15 | 5.91 | 6.37 | 24.74 | |
| 17 | $C_{27}H_{36}N_2O \cdot HCl$ | 441.1 | 73.53 | 8.46 | 6.35 | 8.04 | |
| | | | 73.42 | 8.40 | 6.31 | 8.11 | |
| 18 | $C_{22}H_{25}N_2OF_3Cl_2$ | 461.4 | 57.28 | 5.46 | 6.07 | | 12.35(F) |
| | | | 57.36 | 5.50 | 5.99 | | 12.26 |
| 19 | $C_{22}H_{25}N_2OCl \cdot HCl$ | 407.4 | 64.86 | 6.93 | 6.88 | 17.41 | |
| | | | 64.91 | 6.93 | 6.86 | 17.41 | |
| 20 | $C_{22}H_{24}N_3O_3F_3$ | 435.5 | 60.68 | 5.56 | 9.65 | | 13.09(F) |
| | | | 60.55 | 5.60 | 9.58 | | 13.04 |

NOTE:
Analysis of salts of the carbazole amides was difficult due to hygroscopicity and analysis of their free bases was complicated by their non-crystalline nature and consequential occlusion of dichloromethane.

EXAMPLE 21

Tablets were prepared containing 20 mg of the compound of Example 1 or 6 and sufficient excipient of lactose, starch, talc and magnesium stearate for a final weight of 150 mg.

PHARMACOLOGICAL DATA

The anti-oedematous properties of the compounds were assessed by utilization of a modification of the carrageenin-induced oedema procedure [Proc. Soc. Exp. Biol. Med., 1962, Vol. 11, 544] following administration to male Wistar rats. The data in the following Table display the percentage inhibition by weight compared to control after a dose of 100 mg/kg p.o. or 50 mg/kg i.p.

| Example | Inhibition |
|---|---|
| 1 | 87.7 (i.p.), 14.1 (p.o.) |
| 2 | 82.3 (i.p.), 34.8 (p.o.) |
| 3 | 57.4 (i.p.), 12.9 (p.o.) |
| 5 | 36.4 (p.o.) |
| 6 | 43.6 (p.o.) |
| 7 | 16.5 (p.o.) |
| 8 | 40.8 (p.o.) |
| 9 | 28.7 (p.o.) |
| 10 | 15.1 (p.o.) |
| 11 | 18 (p.o.) |
| 12 | 13 (p.o.) |
| 13 | 17 (p.o.) |
| 14 | 15 (p.o.) |
| 15 | 26 (p.o.) |
| 16 | 19 (p.o.) |
| 17 | 28 (p.o.) |
| 18 | 25 (p.o.) |
| 19 | 24.8 (p.o.) |
| 20 | 5.8 (p.o.) |

Various modifications of the products and process of of the invention may be made without departing from the spirit or scope thereof and it is to be understood that the invention is intended to be limited only as defined in the appended claims.

What is claimed is:

1. A compound selected from the group consisting of alkylaminoamides of the formula

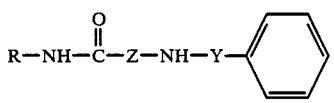

I wherein R is

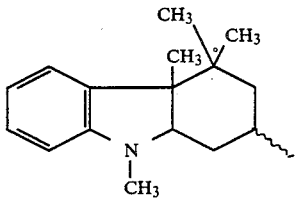

Z is $-(CH_2)_n-$ optionally substituted by an alkyl of 1 to 6 carbon atoms, n is an integer from 1 to 6, Y is $-(CH_2)_n-$ or

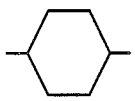

and their non-toxic, pharmaceutically acceptable acid addition salts.

2. A compound of claim 1 wherein R is selected from the group consisting of (1,2,3,4,4a,9a-hexahydro-4,4,4a,9-tetramethylcarbazol-2α-yl) and (1,2,3,4,4a,9a-hexahydro-4,4,4a,9-tetramethylcarbazol-2β-yl); Z is selected from the group consisting of $-CH_2-,-(CH_2)_2-$ and $-(CH_2)_3-$ and Y is selected from the group consisting of

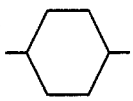

$-(CH_2)_3-$ and $-(CH_2)_4-$.

3. A compound of claim 1 wherein R is selected from the group consisting of (1,2,3,4,4a,9a-hexahydro-4,4,4a,9-tetramethylcarbazol-2α-yl) and (1,2,3,4,4a,9a-hexahydro-4,4,4a,9-tetramethylcarbazol-2β-yl); Z is selected from the group consisting of $-(CH_2)_2-$ and Y is selected from the group consisting of

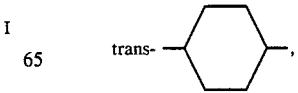

or $-(CH_2)_4-$.

4. A compound of claim 1 selected from the group consisting of N-(1,2,3,4,4a,9a-hexahydro-4,4,4a,9-tetramethylcarbazol-2β-yl)-3-(trans-4-phenylcyclohexylamino)-propionamide; N-(1,2,3,4,4a,9a-hexahydro-4,4,4a,9-tetramethylcarbazol-2β-yl)-2-(trans-4-phenylcyclohexylamino)-acetamide; N-(1,2,3,4,4a,9a-hexahydro-4,4,4a,9-tetramethylcarbazol-2α-yl)-3-(4-phenylbutylamino)-propionamide; N-(1,2,3,4,4a,9a-hexahydro-4,4,4a,9-tetramethylcarbazol-2β-yl)-3-(3-phenylpropylamino)-propionamide; N-(1,2,3,4,4a,9a-hexahydro-4,4,4a,9-tetramethylcarbazol-2α-yl)-2-(4-phenylbutylamino)-acetamide; and their non-toxic, pharmaceutically acceptable acid addition salts.

5. An antiedematous and anti-inflammatory composition comprising an antiedematously and anti-inflammatorily effective amount of at least one compound of claim 1 and an excipient.

6. A composition of claim 5 wherein R is selected from the group consisting of (1,2,3,4,4a,9a-hexahydro-4,4,4a,9-tetramethylcarbazol-2α-yl) and (1,2,3,4,4a,9-hexahydro-4,4,4a,9-tetramethylcarbazol-2β-yl); Z is selected —(CH₂)₂— and —(CH₂)₃— Y is selected from the group consisting of

—(CH₂)₃— and —(CH₂)₄—.

7. A composition of claim 5 wherein R is selected from the group consisting of (1,2,3,4,4a,9a-hexahydro-4,4,4a,9-tetramethylcarbazol-2α-yl) and (1,2,3,4,4a,9a-hexahydro-4,4,4a,9-tetramethylcarbazol-2β-yl); Z is selected from the group consisting of —(CH₂)₂— and Y is selected from the group consisting of

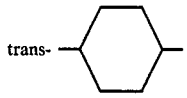

or —(CH₂)₄—.

8. A composition of claim 5 wherein the active compound is selected from the group consisting of N-(1,2,3,4,4a,9a-hexahydro-4,4,4a,9-tetramethylcarbazol-2β-yl)-3-(trans-4-phenylcyclohexylamino)-propionamide; N-(1,2,3,4,4a,9a-hexahydro-4,4,4a,9-tetramethylcarbazol-2β-yl)-2-(trans-4-phenylcyclohexylamino)-acetamide; N-(1,2,3,4,4a,9a-hexahydro-4,4,4a,9-tetramethylcarbazol-2α-yl)-3-(4-phenylbutylamino)-propionamide; N-(1,2,3,4,4a,9a-hexahydro-4,4,4a,9-tetramethylcarbazol-2β-yl)-3-(3-phenylpropylamino)-propionamide; N-(1,2,3,4,4a,9a-hexahydro-4,4,4a,9-tetramethylcarbazol-2α-yl)-2-(4-phenylbutylamino)-acetamide; and their non-toxic, pharmaceutically acceptable acid addition salts.

9. A method of treating edema and inflammation in warm-blooded animals comprises administering to warm-blooded animals an antiedematously and anti-inflammatorily effective amount of at least one compound of claim 1.

10. A method of claim 9 wherein R is selected from the group consisting of (1,2,3,4,4a,9a-hexahydro-4,4,4a,9-tetramethylcarbazol-2α-yl) and (1,2,3,4,4a,9a-hexahydro-4,4,4a,9-tetramethylcarbazol-2β-yl); Z is selected from the group consisting of —CH₂—, —(CH₂)₂— and —(CH₂)₃— and Y is selected from the group consisting of

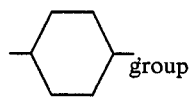

—(CH₂)₃— and —(CH₂)₄—.

11. A method of claim 9 wherein R is selected from the group consisting of (1,2,3,4,4a,9a-hexahydro-4,4,4a,9-tetramethylcarbazol-2α-yl) and (1,2,3,4,4a,9a-hexahydro-4,4,4a,9-tetramethylcarbazol-2β-yl); Z is selected from the group consisting of —(CH₂)₂— and Y is selected from the group consisting of

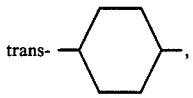

or —(CH₂)₄—.

12. A method of claim 9 wherein the compound is selected from the group consisting of N-(1,2,3,4,4a,9a-hexahydro-4,4,4a,9-tetramethylcarbazol-2β-yl)-3-(trans-4-phenylcyclohexylamino)-propionamide; N-(1,2,3,4,4a,9a-hexahydro-4,4,4a,9-tetramethylcarbazol-2β-yl)-2-(trans-4-phenylcyclohexylamino)-acetamide; N-(1,2,3,4,4a,9a-hexahydro-4,4,4a,9-tetramethylcarbazol-2α-yl)-3-(4-phenylbutylamino)-propionamide; N-(1,2,3,4,4a,9a-hexahydro-4,4,4a,9-tetramethylcarbazol-2β-yl)-3-(3-phenylpropylamino)-propionamide; N-(1,2,3,4,4a,9a-hexahydro-4,4,4a,9-tetramethylcarbazol-2α-yl)-2-(4-phenylbutylamino)-acetamide; and their non-toxic, pharmaceutically acceptable acid addition salts.

* * * * *